United States Patent [19]

Turriff et al.

[11] Patent Number: 5,343,771
[45] Date of Patent: Sep. 6, 1994

[54] TOOL FOR SAMPLING SOIL CONTAINING VOLATILE ORGANIC COMPOUND

[75] Inventors: David E. Turriff, Green Bay; JoAnn L. Johnson, Denmark; Lloyd E. Jacobs; Nils K. Melberg, both of Green Bay, all of Wis.

[73] Assignee: En Chem, Inc., Green Bay, Wis.

[21] Appl. No.: 915,309

[22] Filed: Jul. 20, 1992

[51] Int. Cl.$^5$ ............................................. G01N 1/08
[52] U.S. Cl. ............................... 73/864.44; 73/864.91; 175/20
[58] Field of Search ........... 73/864.44, 864.45, 864.91; 172/21, 22; 175/20, 58, 244, 321, 249

[56] References Cited

U.S. PATENT DOCUMENTS

| | | | |
|---|---|---|---|
| D. 269,844 | 7/1983 | Hackerson | D8/7 |
| 1,109,446 | 9/1914 | Melberg . | |
| 1,162,901 | 12/1915 | Cantey . | |
| 2,643,858 | 6/1953 | Hardman | 255/1.4 |
| 2,664,269 | 12/1953 | Knight et al. | 73/84 |
| 3,146,838 | 9/1964 | Tijmann et al. | 175/405 |
| 3,176,053 | 3/1965 | DiStasio | 264/31 |
| 3,224,512 | 12/1965 | Alexander | 173/19 |
| 3,326,049 | 6/1967 | Eley | 73/429 |
| 3,444,938 | 5/1969 | Ballmann | 73/864.44 |
| 3,497,018 | 2/1970 | Schultz et al. | 175/6 |
| 3,707,197 | 12/1972 | Walesch et al. | 175/20 |
| 4,096,749 | 6/1978 | Stewart | 73/425.2 |
| 4,116,247 | 9/1978 | Zanasi | 141/392 |
| 4,549,612 | 10/1985 | Cushing | 175/20 |
| 4,653,336 | 3/1987 | Vollweiler | 73/864.44 |
| 4,819,735 | 4/1989 | Puckett | 172/22 |
| 4,840,517 | 6/1989 | Bullivant | 175/20 |
| 4,848,484 | 9/1989 | Clements | 175/20 |
| 4,860,599 | 8/1989 | Griffis | 73/864.44 |
| 4,887,413 | 12/1989 | Truckey, Jr. | 53/520 |
| 4,888,999 | 12/1989 | Kozak | 73/864.44 |
| 4,989,678 | 2/1991 | Thompson | 175/20 |
| 5,005,433 | 4/1991 | Patton | 73/864.44 |

Primary Examiner—Hezron E. Williams
Assistant Examiner—Nashmiya Ashraf
Attorney, Agent, or Firm—Jansson & Shupe, Ltd.

[57] ABSTRACT

The invention is an improvement in a soil sampling tool of the type having a handle and a cylindrical sampling barrel with an aperture in the upper end. An ejector extends through the aperture and is attached to a plunger for urging the soil sample out of the barrel. In the improvement, the ejector and aperture define an annular clearance between them so that when a soil sample is taken (and the plunger thereby urged toward the barrel upper end), air can exhaust from the barrel. The plunger includes a boss which extends into and seals the aperture when the plunger is at or near its uppermost position. In that way, vapors of volatile organic compounds are prevented from escaping through the aperture. The tool also includes a cap for sealing the lower end of the barrel so that such vapors cannot escape from the barrel. The improved tool is particularly useful for taking and later analyzing soil samples relating to possible leaking underground storage tanks which contain or have contained petroleum distillates, e.g., gasoline or kerosene.

9 Claims, 7 Drawing Sheets

TOOL FOR SAMPLING SOIL CONTAINING VOLATILE ORGANIC COMPOUND

FIELD OF THE INVENTION

This invention relates generally to devices used for testing and, more particularly, to devices used for soil testing.

BACKGROUND OF THE INVENTION

Soil sampling tools and devices are used for a variety of purposes, e.g., to obtain samples for soil moisture content or to sample a volatile organic compound (VOC) which may have permeated the soil. Sometimes a soil "coring" tool is used simply to explore for buried coins and the like. Examples of such tools are shown in U.S. Pat. Nos. 3,326,049 (Eley); 4,989,678 (Thompson) and 3,707,197 (Walesch et al.).

The device shown in the Eley patent has a barrel with air vent and a shaft threaded to the barrel. The shaft is graduated so that when turned, the soil sample is ejected in increments. The kit shown in the Thompson patent includes a sampling device and a sample containment device, both of which are used for analyzing a soil sample containing a VOC. The tool shown in the Walesch et al. patent is said to be useful for finding buried coins and the like. Other types of sampling tools and instruments are shown in U.S. Pat. Nos. 1,162,901 (Cantey) and 4,887,413 (Tuckey, Jr.).

It is common knowledge that tanks for storing liquids may, over time, develop a leak. If the tank is above ground, the leak is usually observed rather soon after its onset and not much damage results. On the other hand, there is an already-substantial and growing awareness that certain types of liquid storage tanks placed underground have a greater-than-normal propensity to deteriorate and leak. Such types include tanks made of common sheet steel from which protective coatings have either been eaten away or were non-existent. And a substantial factor contributing to the risk of tank leakage is that with an underground tank, leakage is not visible. Usually, such leakage can only be detected by excavation and testing.

And the risks are enormous. Undetected leaks of underground storage tanks can and do contaminate soil and potable water supplies, the latter by polluting underground aquifers from which a great deal of drinking water is drawn. Recent legislation recognizes risks presented by leaking underground storage tanks and provides for remediation of damage caused by such leaks. Because of the number of gasoline service stations and private fuel and solvent storage tanks, leakage of petroleum distillates and hydrocarbons is a particularly significant problem.

Good remediation requires that personnel be able to accurately determine the nature and extent of the leak. Such determination depends in large part upon the availability of high quality test instruments. The efforts of earlier workers in this regard have not been entirely satisfactory. For example, the Thompson patent emphasizes speed of transfer of a soil sample from a sampling tool to a containment device to minimize loss of VOC. This is clearly an impractical solution to retention of sample integrity, especially if the leaky tank was installed at a site distant from the analyst's laboratory. Earlier sampling tools fail to offer solutions reducing the substantial storage space required to transport dozens of tools to and from a site.

Establishing sample custody (through records relating a particular sample to a particular locale and, later, to a particular laboratory vial) is yet another aspect of good testing practice to which earlier tools have not been particularly responsive. An improved sampling tool which maintains sample integrity, which minimize required space and which helps establish a chain of custody would clearly be an important advance in the art.

OBJECTS OF THE INVENTION

It is an object of the invention to provide an improved soil sampling tool overcoming some of the problems and shortcomings of the prior art.

Another object of the invention is to provide an improved soil sampling tool which preserves the integrity of a soil sample permeated with a VOC.

Yet another object of the invention is to provide an improved soil sampling tool which avoids sample contamination.

Another object of the invention is to provide an improved soil sampling tool which is readily urged into various types of soil.

Still another object of the invention is to provide an improved soil sampling tool aiding in establishing a sample chain of custody.

Another object of the invention is to provide an improved soil sampling tool which can be inserted into a VOC vial while yet preserving sample integrity. How these and other objects are accomplished will become apparent from the following descriptions and the drawing.

SUMMARY OF THE INVENTION

The invention is an improvement in a soil sampling tool of the type having a handle, a cylindrical sampling barrel with an aperture in one end of the barrel. An ejector is movable to extend through the aperture and is attached to an ejector-driven plunger which moves within the barrel. When a soil sample is taken by inserting the barrel mouth into soil, the plunger is urged along the barrel toward the aperture.

In the improvement, the ejector and aperture define an air exhaustion clearance between them so that air is not trapped in the barrel and the plunger may freely move toward the aperture. The plunger includes a boss which extends into and seals the aperture. VOC vapors are thereby restricted from escaping through the aperture. While various sealing arrangements are possible, in the preferred tool, the aperture includes a perimeter and the boss includes a ring (such as a resilient O-ring) sealing against the perimeter.

The plunger is movable within the barrel between what may be described as a sample-extracting position and a sample-ejecting position. In a variation of the embodiment described above, the plunger is spring-biased to the sample-extracting position for sealing the aperture, thus preventing VOC vapors from escaping through it.

Usually, it is desirable to entirely confine soil-entrained VOC vapors within the barrel. Accordingly, the barrel includes a mouth portion defining a barrel mouth and the tool preferably includes a cap in sealing engagement with the mouth portion to prevent vapor escape. A preferred cap is cup-like in construction and has an interior cavity and a cavity wall. The cap cavity has a cross-sectional shape generally conforming to that of the barrel which, in the preferred embodiment, is cylindrical. Fitted into a circumferential groove in the cavity wall is a ring, e.g., a resilient O-ring, which seals against the mouth portion when the cap is placed thereon.

The stud and its ring are cooperatively sized with the aperture perimeter so that a tight seal is formed. Similarly, the cap and its ring and the barrel mouth portion are cooperatively sized for a tight seal. With reasonably close-tolerance machining, no seal lubricant is required. However, if needed, a seal lubricant may be used. When taking samples of soil possibly contaminated with VOCs, impairment of the sample (or contamination of any VOC therein) must be avoided. For that reason, the presence of a petroleum-based tool lubricant is to be avoided.

Accordingly, both the boss ring and the cap ring may have a non-petroleum lubricant applied to them to help avoid such contamination. A highly preferred lubricant is powdered graphite.

When testing soil for the presence of a contaminant such as VOCs, it is not unusual to take several dozen individual soil samples. Such samples ("captured" within the tool barrel) must then be taken to a remote laboratory for analysis. Clearly, provision of adequate storage and carrying space for several dozen complete tools becomes a significant concern. In a preferred sampling tool, the handle and ejector may be removable from the barrel and plunger, respectively. When removed, the aperture may be plugged for vapor retention. The barrel is thereby prepared for temporary storage of a VOC-bearing soil sample. The amount of space thereby saved is significant. There are other ways to save space, as well. Only samples found to be "positive" by field-screening methods need be preserved for transport to the laboratory. "Negative" samples are ejected from the tool on-site without additional testing.

It is commonly known that soils of a variety of types may be encountered when taking samples at different locales. Some may be hard clay or clay-like soils which resist tool barrel insertion. The preferred tool includes a plurality of handles, one of which is generally T-shaped for forcefully urging the barrel into soil.

Good sampling practice indicates that those persons taking and analyzing samples be able to establish a "chain of custody" for the sample. That is, they should be able to demonstrate that a particular sample was taken from a particular locale and deposited for analysis into a particular vial. Further, they may be required to demonstrate, by use of a site map or sketch, that a sample was taken from a particular spot at the locale.

A preferred sampling tool includes a sample designator, e.g., an alpha, numeric or alpha-numeric code designator, marked thereon whereby a chain of custody may be established with respect to a soil sample. That is, a spot on a site map and a sample-receiving vial are marked with the same designator as appears on a particular tool so that the tool "links" the spot and the vial. Sampling tools used for VOC testing are (or should be) washed frequently and subjected to some abuse. Therefore, preferred marking is by engraving or otherwise marking the designator on the tool, e.g., on the tool barrel.

When depositing the sample into a laboratory vial for analysis, there is a possibility that some VOC vapors could escape during handling. This would affect the accuracy of the analysis. A preferred tool has a barrel which is generally cylindrical and has an outside diameter not in excess of 25 millimeters. When so configured, the barrel may be inserted into the opening of a VOC vial with very slight clearance between the barrel and the vial. Such arrangement helps prevent significant vapor loss.

Other aspects of the invention are set forth in the following detailed description and the drawing.

DETAILED DESCRIPTIONS OF PREFERRED EMBODIMENTS

The improved soil sampling tool 10 is particularly useful in collecting soil samples 11 permeated with a VOC. As described below, the tool 10 has new features facilitating sample preservation, storage, transportation and identification. Such features will be welcomed by those having responsibilities for leak-site analysis and remediation.

Figure 1:
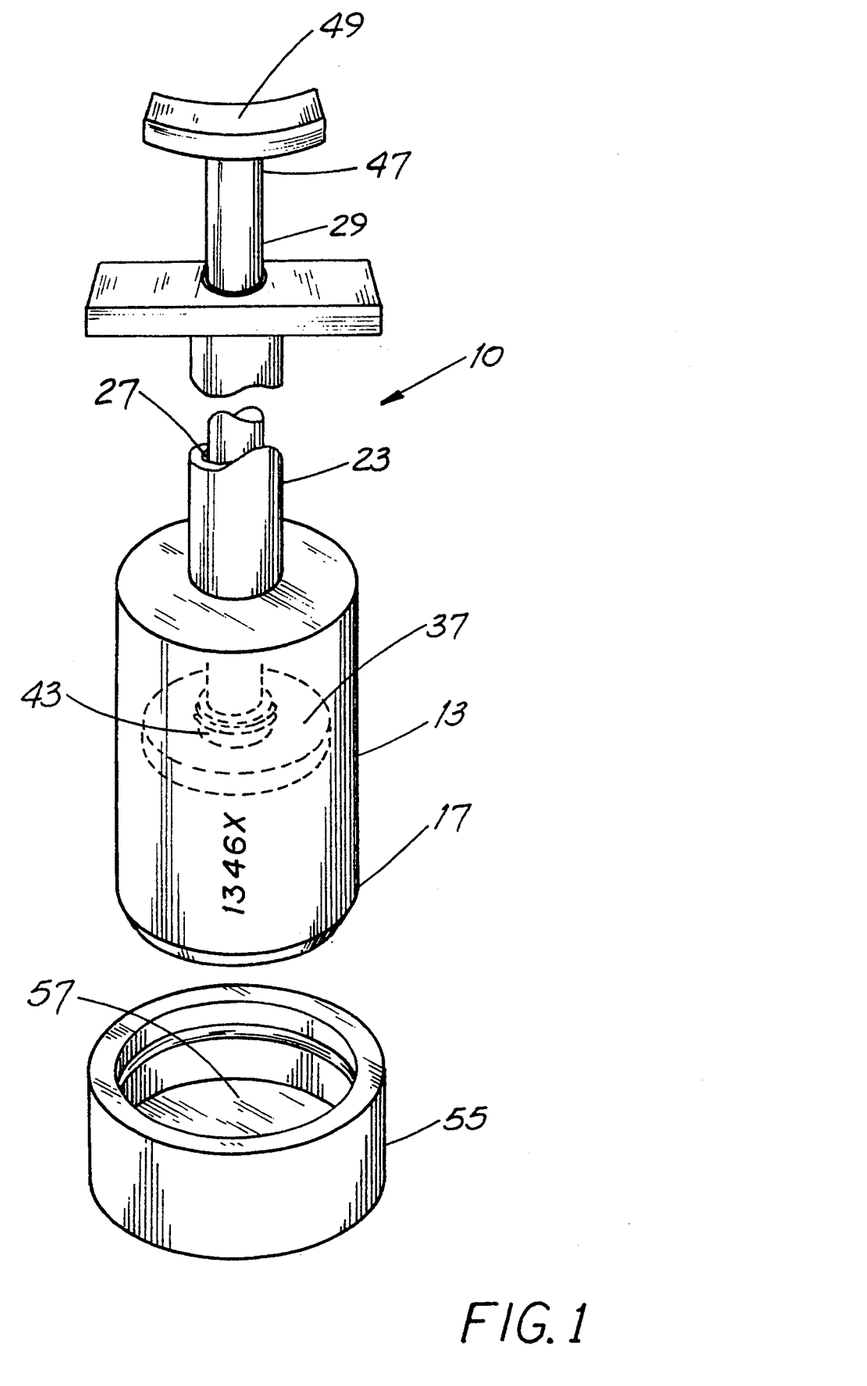
FIG. 1 is a perspective view of an embodiment of the improved tool with parts broken away and other parts shown in phantom outline.
Figure 2:
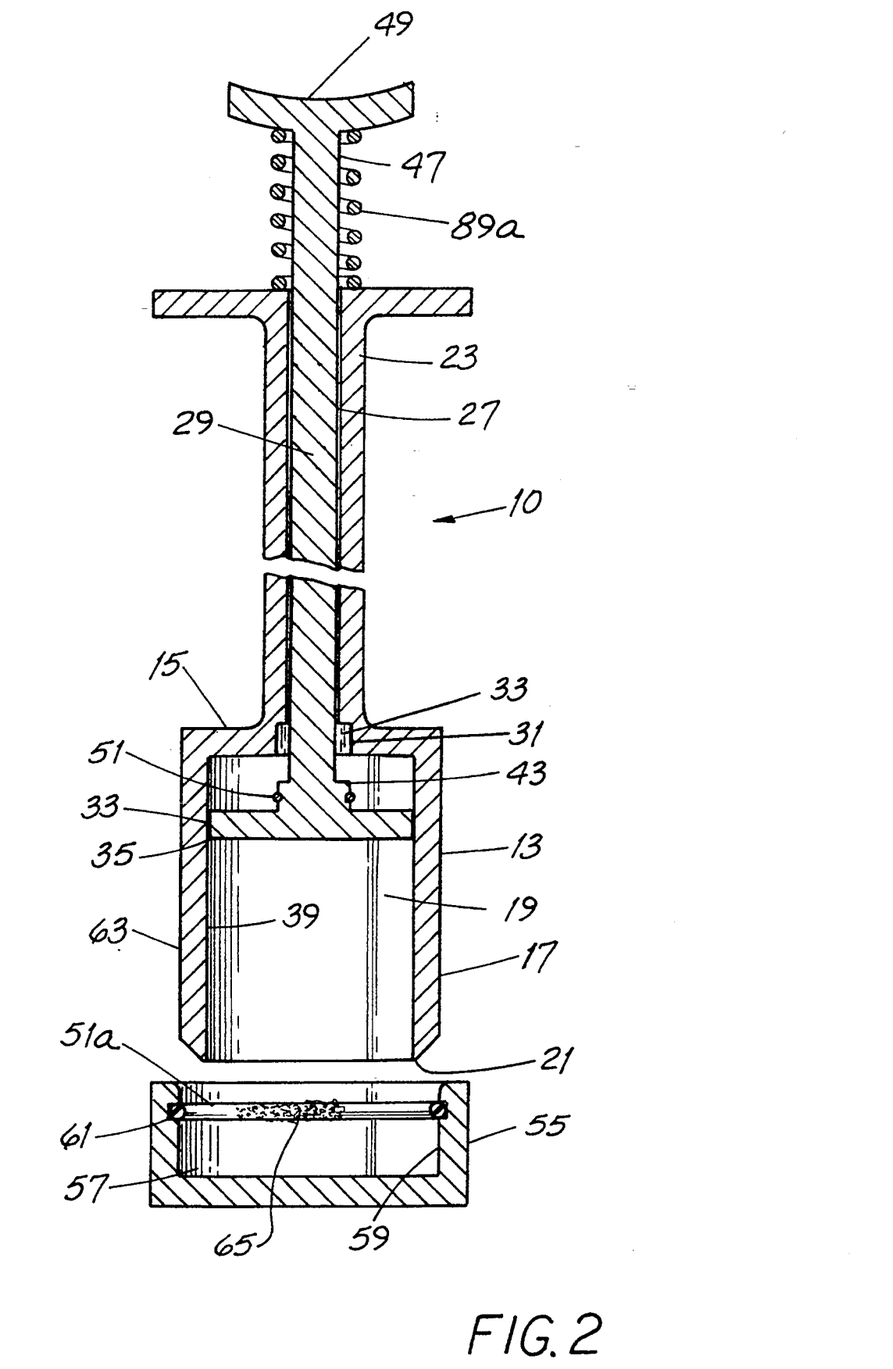
FIG. 2 is, generally, a cross-sectional view of the tool of FIG. 1 taken along a viewing plane coincident with the longitudinal tool axis, with parts broken away and other parts shown in full representation.

Referring first to FIGS. 1 and 2, the improved sampling tool 10 includes a hollow, generally cylindrical barrel 13 having an end wall 15 and a mouth portion 17. The interior region 19 of the barrel 13 is of generally uniform diameter along its length and has a volumetric capacity of 25-30 grams, for example The edge 21 of the mouth portion 17 is bevelled inward, resulting in a relatively sharp soil-cutting "blade."

Figure 4:
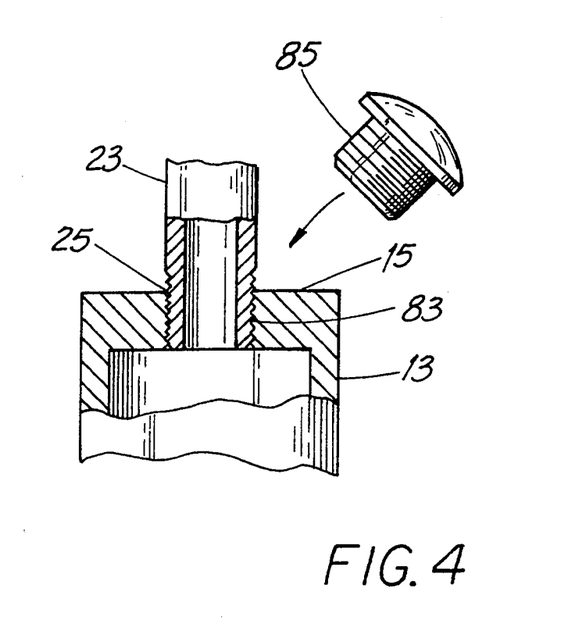
FIG. 4 is a cross-sectional side elevation view, with parts broken away, showing a variation of a portion of the tool of FIG. 1.

An elongate, tube-like handle 23 is concentrically attached to the barrel end wall 15. In a preferred embodiment, the handle 23 is separably attached to the end wall 15 (by a threaded connection 25, for example as shown in FIG. 4) so that the handle 23 and barrel 13 can be readily attached to and detached from one another for purposes described below. The T-shaped handle shown in FIGS. 1 and 2 is preferred in situations where soil samples 11 are expected to be taken from dense, relatively hard soils such as clay soils. The T-shaped handle 23 affords an opportunity to apply a substantial insertion force to the tool 10.

The handle 23 has a passage 27 extending along its length for receiving a rod-like ejector 29 and the handle 23, passage 27 and ejector 29 are preferably circular in cross-sectional shape. The diameters of the passage 27 and the ejector 29 are cooperatively selected to provide slight clearance therebetween so that the ejector 29 may move freely within the passage 27.

As best seen in FIG. 2, the barrel 13 has an end aperture 31 and the ejector 29 and aperture 31 define an air exhaustion clearance 33 between them. Since there is just enough space between the rim 35 of the plunger 37 and the interior wall 39 of the barrel 13 to permit relatively free sliding plunger movement, such clearance 33 permits air to escape along the passage 27 as the tool 10 is urged into soil and the plunger 37 is thereby driven toward the end wall 15.

Figure 3:
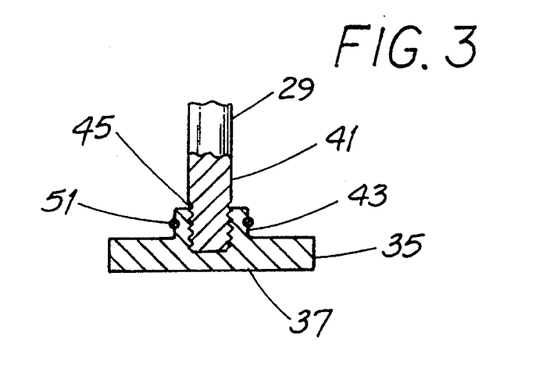
FIG. 3 is a side elevation view, partly in cross-section, of the tool plunger and ejector.
Figure 5:
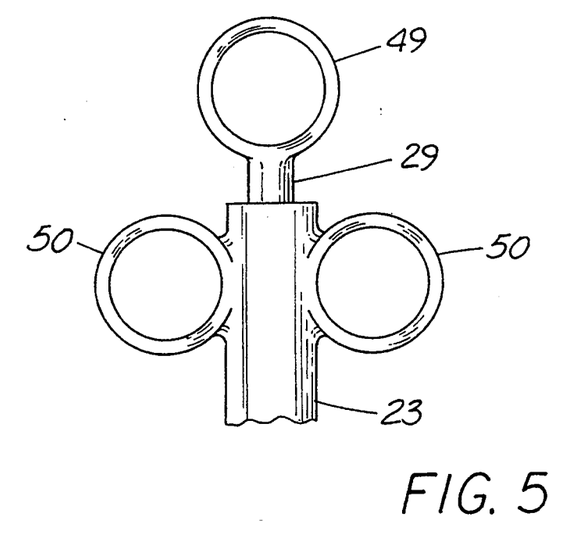
FIG. 5 is a side elevation view, with parts broken away, showing a variation of another portion of the tool of FIG. 1.

Referring additionally to FIG. 3, a disc-like plunger 37 is mounted to the distal end 41 of the ejector 29 and has a boss 43 extending a short distance from the plunger 37. For reasons described below, the ejector 29 and plunger 37 are preferably readily attachable to and detachable from one other. In the illustrated exemplary embodiment, the boss 43 has a threaded pocket 45 and the ejector distal end 41 is similarly threaded for attachment to the boss 43. At its proximal end 47, the ejector 29 includes a thumb engagement member 49 so that when the handle 23 and member 49 are grasped "hypodermic fashion," the member 49 may be depressed toward the handle 23 to eject a soil sample 11 from the barrel 13. And as shown in FIG. 5, the thumb engagement member 49 may be ring-like in shape and a handle 23 with side rings 50 may be provided instead of the T-shaped handle 23 shown in FIGS. 1 and 2.

Since such samples 11 are usually transported to a laboratory for analysis, it is highly preferred that VOC vapors be prevented from escaping from the sample 11 and from the tool 10 through the aperture 31. Diminution of the amount of vapor and VOC present in the sample 11 will "skew" the test results and may cause the level of soil contamination to appear less than it actually is. Accordingly, the plunger boss 43 seals the aperture 31 when the plunger 37 is closely adjacent to or in contact with the barrel end wall 15. Sealing is by a resilient O-ring 51 seated in a circumferential groove in the outer surface of the boss 43.

Figure 9:
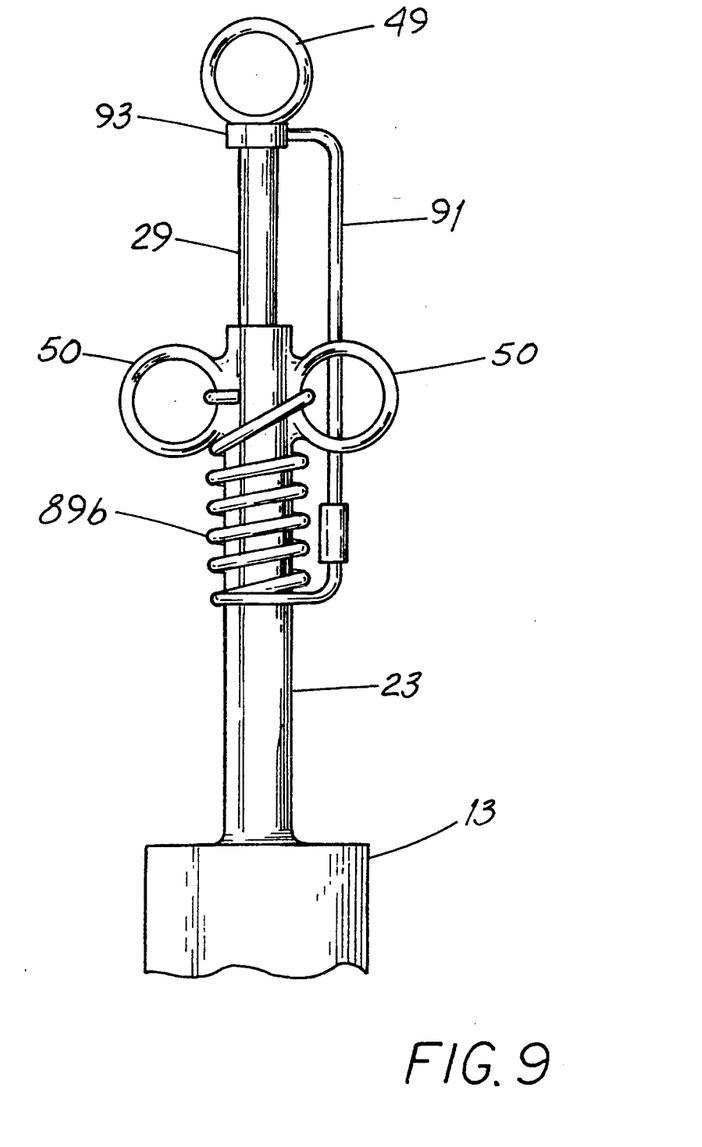
FIG. 9 is a side elevation view of a variation of the tool including a biasing spring.

It is highly preferred that the aperture 31 be sealed even as the tool barrel 13 starts penetrating into the soil. In the embodiments described above, the plunger 37 may be spaced away from the barrel end wall 15 when penetration starts, especially if the tool 10 is prior held with the barrel 13 downward. Referring to FIGS. 1 and 9, the plunger 37 is biased by a spring 89a or 89b to the sample-extracting position, i.e., that position at which the plunger 37 seals the aperture 31. In that way, VOC vapors are prevented from escaping through the aperture, especially at the onset of sample "cutting."

In the arrangement of FIG. 1, the compression spring 89a is interposed between the handle 23 and the thumb engagement member 49. In the arrangement of FIG. 9, the tension spring 89b is attached to and extends from the side rings 50 downward (as viewed in FIG. 9) along the handle 23. A coupler rod 91 extends between the lower end of the spring 89b and a collar 93 immediately below the member 49. In each instance, the spring 89a, 89b biases the ejector 29 and its plunger 37 upward to seal the aperture 31. The aperture 31 may be sealed by an O-ring 51 on the plunger boss 43 as described below.

Figure 10:
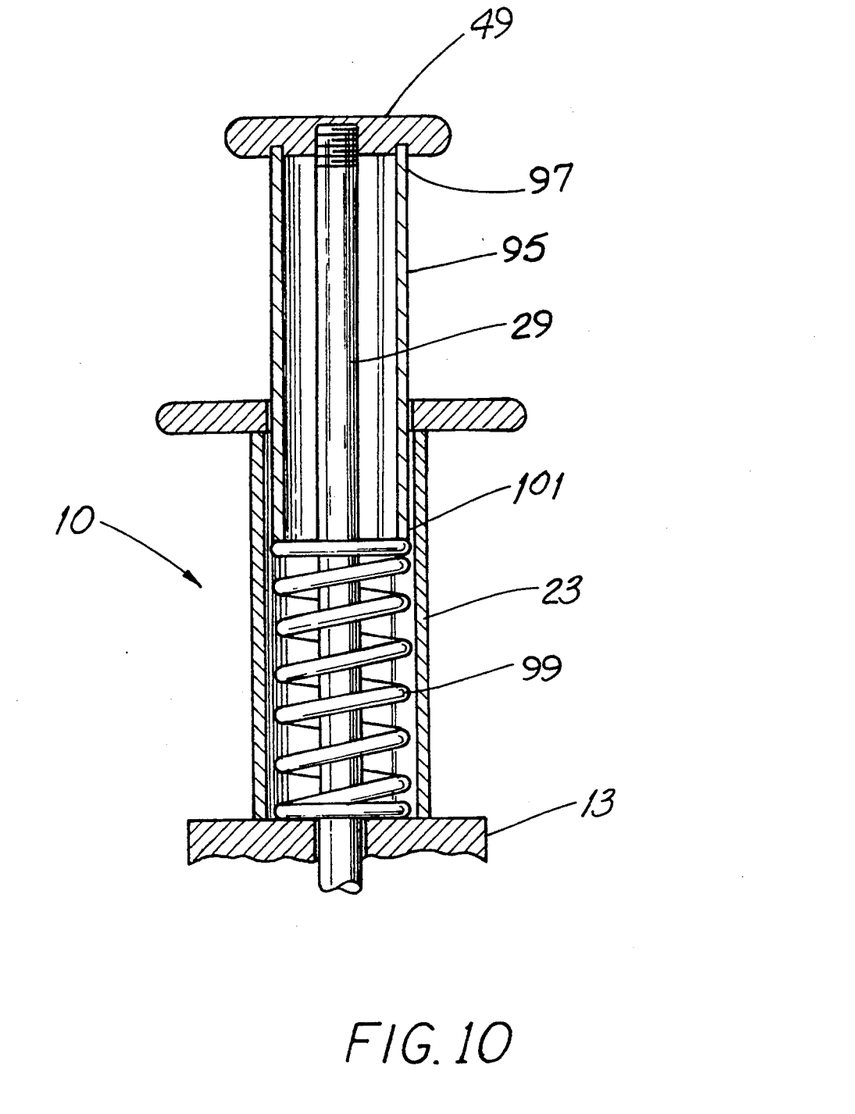
FIG. 10 is a side elevation view, partly in cross-section and with parts broken away, of another variation of the tool including a biasing spring.

In the arrangement of FIG. 10, the tool 10 includes a hollow tube 95 received telescope-fashion in the handle 23. The upper end 97 of the tube 95 is attached to a thumb engagement member 49 as is the ejector 29. A compression spring 99 is confined between the lower end 101 of the tube 95 and the top of the barrel 13. The spring 99 biases the tube 95, member 49 and ejector 29 upward in the absence of downward force on the member 49.

Figure 8:
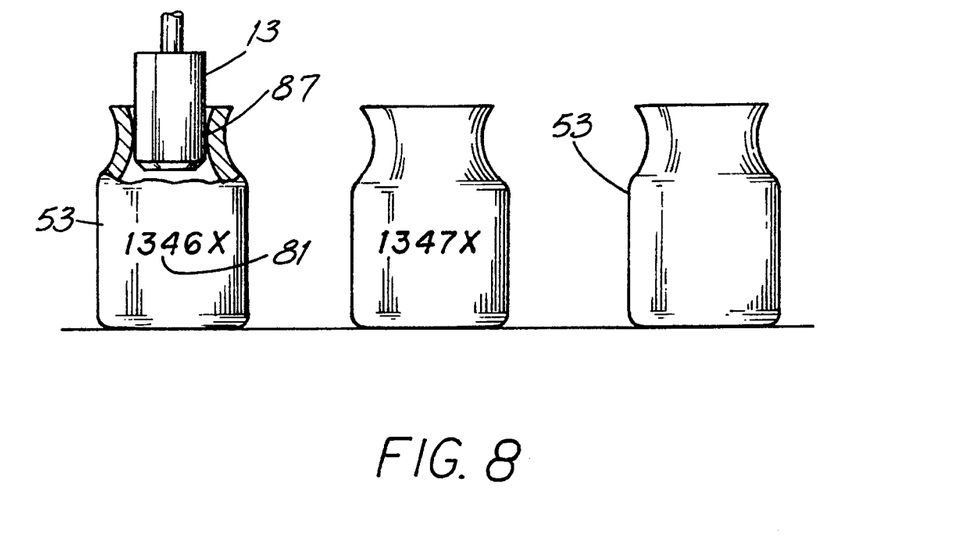
FIG. 8 illustrates how a soil sample is ejected into a vial for later sample analysis.

Referring further to FIGS. 1 and 2 and to FIG. 8, it is preferred that the barrel interior region 19 be completely sealed after a soil sample 11 is taken but before the sample 11 is ejected to a vial 53 for sample analysis. To that end, the improved tool 10 also includes a cup-like cap 55 which has an interior cavity 57 and a cavity wall 59. The cap cavity 57 has a cross-sectional shape generally conforming to that of the barrel 13 which, in the preferred embodiment, is cylindrical. A resilient O-ring 51a is seated in a circumferential groove 61 formed in the cavity wall 59. Such O-ring 51a helps assure a vapor-tight seal against the mouth portion 17 when the cap 55 is placed on such portion 17.

It should be understood that sealing the barrel interior region 19 can be accomplished in other ways. For example, the boss 43 and aperture 31 can be formed to permit very closely fitted, sliding clearance between them and thereby provide a relatively good vapor seal. The barrel outer wall 63 and the cap cavity wall 59 can be similarly formed. However, use of O-ring seals 51, 51a permits some "forgiveness" in certain manufacturing dimensional tolerances and should result in a reduced manufacturing cost.

As explained in the summary, when O-rings 51, 51a are used for sealing, some difficulty may be experienced in positioning the sealing "pieces" (the boss 43 or the cap 55) to a fully seated position if the pieces are not made to close tolerances. If needed, a seal lubricant 65 may be applied to the rings 51, 51a and nearby surfaces to help avoid such difficulty. However, care must be taken to avoid sample contamination by a petroleum-based product such as a lubricating oil. Therefore, a highly preferred lubricant 65 is powdered graphite.

Figure 6:
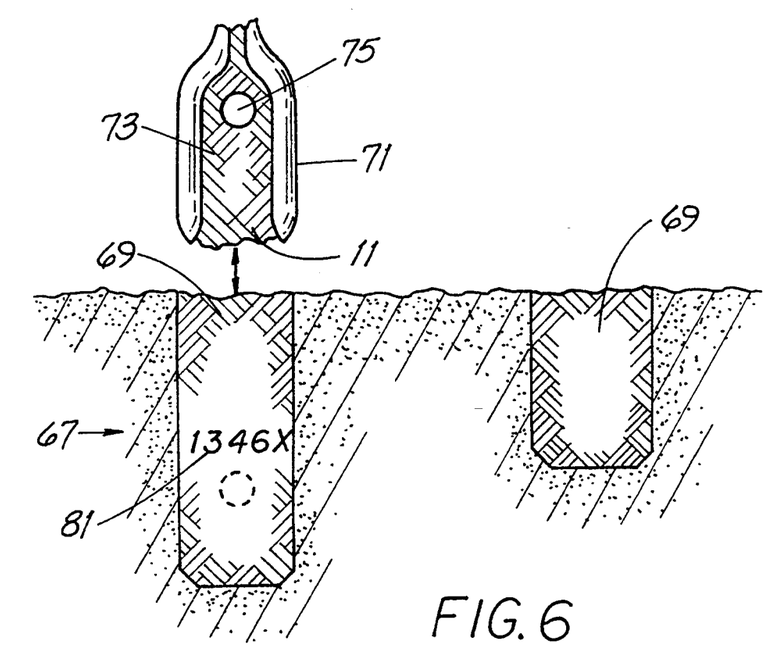
FIG. 6 is a representative cross-sectional side elevation view of a suspected leaky underground storage tank site which is to be analyzed using bored holes.

The following is an explanation of how and where soil samples 11 are taken and identified and how such samples 11 are handled in preparation for lab analysis. It is assumed that the site 67 of a suspected leaking underground storage tank has been identified and such site 67 is shown generally in FIGS. 6 and 7. As shown in FIG. 6, those involved in determining whether and to what extent contamination exists at the site 67 will bore holes 69 (to avoid sampling at the earth surface where VOC and vapors may be less concentrated) and use what is known as a split spoon device 71 (resembling a "plunge type" post hole digger) to extract relatively large "slugs" 73 of soil from various holes 69. Using the tool 10, a soil sample is taken from a location 75 (or perhaps two or more locations) on the slug 73. Each slug 73 is removed at a known depth and from a hole 69 have a known location. Both such informational items are recorded for "mapping" the site 67 with a field sketch.

Figure 7:
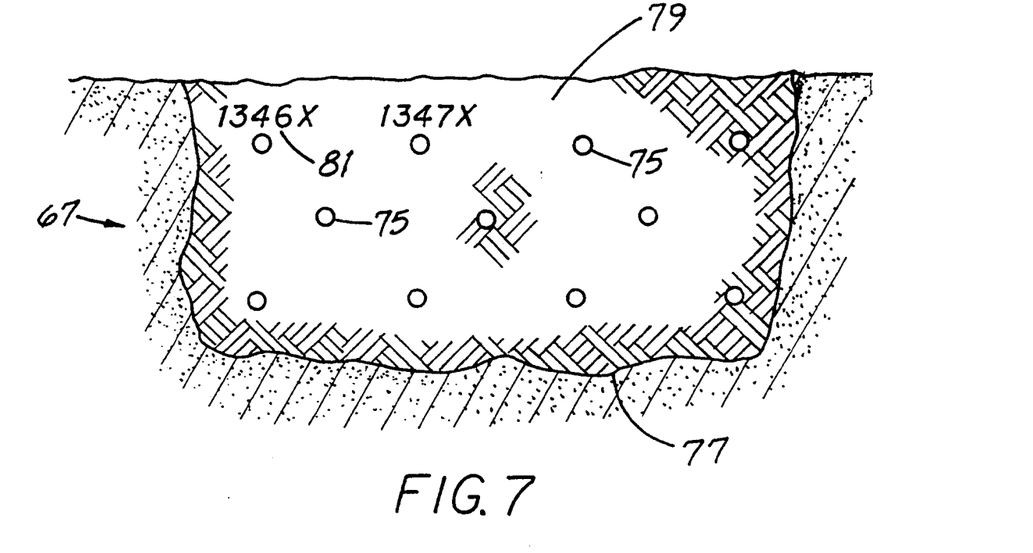
FIG. 7 is a representative cross-sectional side elevation view of a site like that of FIG. 6 which is being analyzed using a dug hole.

Referring to FIG. 7, in another approach, a hole 77 is dug in the earth. Samples are taken at various horizontally and vertically spaced locations 75 along the generally vertical wall 79 of the hole 77 and, probably, at other locations. The wall 79 and the locations 75 will similarly be mapped with a field sketch.

Irrespective of whether bored or dug holes 69, 77 are used, each such sample location 75 is identified on the sketch with a designator 81 which is unique for that site 67. It is likely that soil samples 11 will be taken from several dozen locations 75 at a particular site 67. For reasons that will become apparent, sampling a site 67 therefore involves having a substantial number of tools 10 available, i.e., at least a quantity equal to the number of locations 75.

Referring further to FIG. 7, the designator 81 used for a particular location 75 is that which is marked on the tool 10 used to take that particular sample 11. The designator 81 is preferably prominently marked on the tool 10, e.g., on the barrel. Since a particular tool 10 will be used many times (at different sites 67) and since such tools 10 must be thoroughly washed and cleaned prior to use, marking is preferably permanent by etching, engraving or the like.

Immediately after the sample 11 is taken (and before significant VOC evaporation can occur), the barrel 13 with the possibly-contaminated soil sample 11 inside is then sealed as described above and the tool 10 set aside. The overall length of the tool 10 may be two or three times the length of the barrel 13 alone. Clearly, provision of adequate storage and carrying space for several dozen complete tools 10 becomes a significant concern, especially at a remote field site 67 where working conditions may be less than ideal. In a preferred sampling tool 10, the handle 23 and ejector 29 may be removable from the barrel 13 and plunger 37, respectively. When removed, the aperture 83 is plugged for vapor retention using a plug 85 like that shown in FIG. 4. And, of course, "sample loaded" tools 10 can be stored as is without removing the handle 23 and ejector 29.

Referring to FIG. 8, when all desired samples 11 have been taken, the "sample-loaded" tools 10 are used to place soil samples 11 into vials 53 kept on site 67. Such samples 11 are later analyzed at a laboratory. And each sample 11 is placed into a vial 53 marked with the same designator 81 as is marked on the tool 10 and on the field sketch. The tool 10 thereby becomes the link between a particular location 75 and a particular vial 53 and helps establish a sample "chain of custody".

Sample placement is by uncapping the barrel 13, quickly inserting such barrel 13 into a vial 53 and manipulating the ejector 29 to drive the sample 11 into the vial 53 for virtually-immediate vial capping. In a highly preferred version, the tool barrel 13 has an outside diameter not in excess of, and preferably very slightly less than, about 25 mm. Since many types of appropriately-sized lab vials 53 have a mouth diameter of 25 mm or greater, such a barrel 13 can be readily inserted into such vials and, of course, into vials 53 having larger mouths. As illustrated in FIG. 8, an appropriately-sized barrel 13 closely fits the diameter of the vial mouth 87 to help prevent vapors from escaping.

While the principles of this invention have been described in connection with specific embodiments, such embodiments are only exemplary. As other examples, different types of handles and thumb engagement members can be used. And the barrel region 19, ejector 29 and plunger 37 need not have a circular cross-sectional shape although for a number of reasons, such shape is preferred. Aperture sealing could be by a seal ring on the upper surface of the plunger 37 and/or the interior surface of the end wall 15. The foregoing variants are considered to be within the scope of the invention and, of course, are not the only such variants.

We claim:

1. In a soil sampling tool having a handle, a cylindrical sampling barrel with an interior region and an enlarged aperture, an ejector movable to extend through the aperture and an ejector-driven plunger movable within the barrel, the improvement wherein:
   the handle is tubular and has an interior wall;
   the ejector and the interior wall define an air exhaustion passage therebetween, such passage extending between the interior region and ambient air;
   the passage terminates in the enlarged aperture which is defined by a perimeter surface;
   the plunger includes a boss having an aperture seal thereon;
   the boss is telescoped within the aperture;
   the aperture seal is between the boss and the aperture perimeter surface and seals the aperture;
   and wherein:
   the tool includes a cap which is hand-removable from the barrel;
   the barrel is closed by the cap capturing a resilient barrel seal between the barrel and the cap,
   whereby vaporized volatile organic compound is prevented from escaping from the barrel.

2. The tool of claim 1 wherein the aperture seal is an O-ring mounted on and moving with the boss and the plunger.

3. The tool of claim 2 wherein the O-ring has a non-petroleum lubricant applied thereto, thereby avoiding contamination of a soil sample.

4. The tool of claim 1 wherein:
   the barrel includes a mouth portion;
   the cap overlaps the mouth portion and has an interior wall retaining the barrel seal.

5. The tool of claim 1 wherein the barrel seal has a non-petroleum lubricant applied thereto, thereby avoiding contamination of a soil sample.

6. The tool of claim 1 wherein:
   the barrel contains a soil sample bearing a volatile organic compound; and
   the soil sample and the volatile organic compound are confined between the plunger and the cap.

7. The tool of claim 1 wherein such tool has a plurality of handles, one of which is generally T-shaped for forcefully urging the barrel into soil.

8. The tool of claim 1 wherein:
   the tool barrel contains a coil sample taken from a particular locale; and
   the tool is marked with a sample designator, whereby the soil sample may be identified to the locale.

9. The tool of claim 8 wherein the sample designator is permanently marked on the tool.

* * * * *